United States Patent
Wong (10) Patent No.: US 9,701,602 B2
(45) Date of Patent: Jul. 11, 2017

(54) EMISSIONS CONTROL OF SPENT AIR FROM CUMENE OXIDATION

(71) Applicant: Kellogg Brown & Root LLC, Houston, TX (US)

(72) Inventor: Eric Wing-Tak Wong, Houston, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 405 days.

(21) Appl. No.: 14/605,792

(22) Filed: Jan. 26, 2015

(65) Prior Publication Data

US 2015/0133702 A1    May 14, 2015

Related U.S. Application Data

(63) Continuation-in-part of application No. 13/776,943, filed on Feb. 26, 2013, now abandoned.

(51) Int. Cl.

| | |
|---|---|
| *B01D 53/72* | (2006.01) |
| *B01D 53/84* | (2006.01) |
| *C07C 29/48* | (2006.01) |
| *C07C 29/50* | (2006.01) |
| *B01D 53/75* | (2006.01) |
| *B01D 53/04* | (2006.01) |
| *B01D 53/14* | (2006.01) |
| *B01D 53/78* | (2006.01) |
| *B01D 53/82* | (2006.01) |
| *B01D 53/26* | (2006.01) |

(52) U.S. Cl.
CPC ............... *C07C 29/48* (2013.01); *B01D 53/72* (2013.01); *B01D 53/75* (2013.01); *B01D 53/84* (2013.01); *C07C 29/50* (2013.01); *B01D 53/04* (2013.01); *B01D 53/1487* (2013.01); *B01D 53/265* (2013.01); *B01D 53/78* (2013.01); *B01D 53/82* (2013.01); *B01D 2251/102* (2013.01); *B01D 2251/11* (2013.01); *B01D 2252/205* (2013.01); *B01D 2252/2026* (2013.01); *B01D 2253/102* (2013.01); *B01D 2253/108* (2013.01); *B01D 2257/704* (2013.01); *B01D 2257/708* (2013.01); *B01D 2257/80* (2013.01)

(58) Field of Classification Search
CPC ......... C07C 29/48; C07C 29/50; B01D 53/72; B01D 53/75; B01D 53/84
See application file for complete search history.

(56) References Cited

U.S. PATENT DOCUMENTS 6,372,021 B1 * 4/2002 Boggs .................. B01D 53/002
568/749

* cited by examiner

*Primary Examiner* — Kara Johnson
(74) *Attorney, Agent, or Firm* — Gary Machetta (57) ABSTRACT

Methods and systems for removing volatile organic compounds from spent air are provided. The method can include oxidizing cumene in the presence of an oxidant to produce an oxidized product containing methanol and a spent air, separating the spent air from the oxidized product, contacting the spent air with an absorbent, an adsorbent, or a mixture thereof to remove at least a portion of any impurities in the spent air to produce a first purified air, and contacting the first purified air with a biological material to produce a treated air.

20 Claims, 2 Drawing Sheets

EMISSIONS CONTROL OF SPENT AIR FROM CUMENE OXIDATION

CROSS-REFERENCE TO RELATED APPLICATIONS

This application is a continuation-in-part of U.S. patent application Ser. No. 13/776,943, filed on Feb. 26, 2013, and claims the benefit of priority from the aforementioned application, the contents of which is incorporated by reference for all purposes.

BACKGROUND

Field

Embodiments described herein generally relate to methods and systems for processing spent air. More particularly, such embodiments relate to methods and systems for cleaning spent air from a cumene oxidation process.

Description of the Related Art

Phenol and acetone are produced in various processes, the most common of which is known as the Hock Process, the Hock and Lang Process, or the cumene-to-phenol process, among others. This process begins with the oxidation of cumene (isopropyl benzene) to form cumene hydro-peroxide (CHP). The oxidation of cumene can result in the discharge of spent air. This spent air usually contains volatile organic components or volatile organic compounds (VOCs), such as unreacted cumene. Health hazards are typically associated with exposure to VOCs and VOC emissions are subject to governmental regulations.

Industry, therefore, has sought to limit the amount of VOCs emitted from cumene oxidation processes. Current industry practice is to condense the cumene in the spent air from a cumene oxidation process with cooling water and/or refrigeration. The condensed cumene is then separated from any remaining gaseous components. These remaining gaseous components are then typically subjected to thermal or catalytic incineration. Other processes include filtering the remaining gaseous components by adsorption and, if required, subjecting the gaseous components to thermal or catalytic incineration. Incinerating the remaining gaseous components, however, can result in NOx emissions.

There is a need, therefore, for improved methods and systems for removing VOCs from the spent air from a cumene oxidation process.

DETAILED DESCRIPTION

Methods and systems for removing VOCs from spent air are provided. The method can include oxidizing cumene in the presence of an oxidant to produce an oxidized product containing methanol and a spent air, separating the spent air from the oxidized product, contacting the spent air with an absorbent, an adsorbent, or a mixture thereof to remove at least a portion of any impurities in the spent air to produce a first purified air, and contacting the first purified air with a biological material to produce a treated air.

It has been surprisingly and unexpectedly found that an incinerator used in treating spent air from a cumene oxidation process can be replaced by one or more bioreactors. Replacing the incinerator with the bioreactor can result in lower maintenance costs. It has also been surprisingly and unexpectedly found that the bioreactor can reduce the concentration of volatile organic compounds and other air pollutants found in the spent air to lower concentrations than incineration of the spent air can achieve. For example, a bioreactor can remove essentially all remaining contaminants from the spent air without incineration resulting in a treated, cleaned, or purified spent air containing essentially no VOCs. As used herein, the phrases "essentially no VOCs" and "essentially free of VOCs" are used interchangeably and refer to a treated, cleaned, or purified spent air containing less than 50 ppmw, less than 30 ppmw, less than 20 ppmw, less than, 15 ppmw, less than 10 ppmw, less than 5 ppmw, less than 3 ppmw, less than 1 ppmw, less than 0.1 ppmw, less than 0.01 ppmw, less than 0.001 ppmw, less than 0.0001 ppmw, or less than 0.00001 ppmw total VOCs. It has also been found that cleaning the spent air with activated carbon or other solid adsorbent(s) can be replaced with liquid solvent absorption, which can significantly reduce operating costs as compared to solid adsorption systems. As used herein, the term "volatile organic compound" or "VOC" refers to any organic compound having a boiling point less than or equal to 250° C. measured at a standard atmospheric pressure of 101.3 kPa. As used herein, the term "non-aromatics" refers to VOCs not containing an aromatic compound or aromatic group. Illustrative VOCs can include, but are not limited to, cumene, non-aromatics, benzene, methanol, toluene, formic acid, or any mixture thereof.

Figure 1:
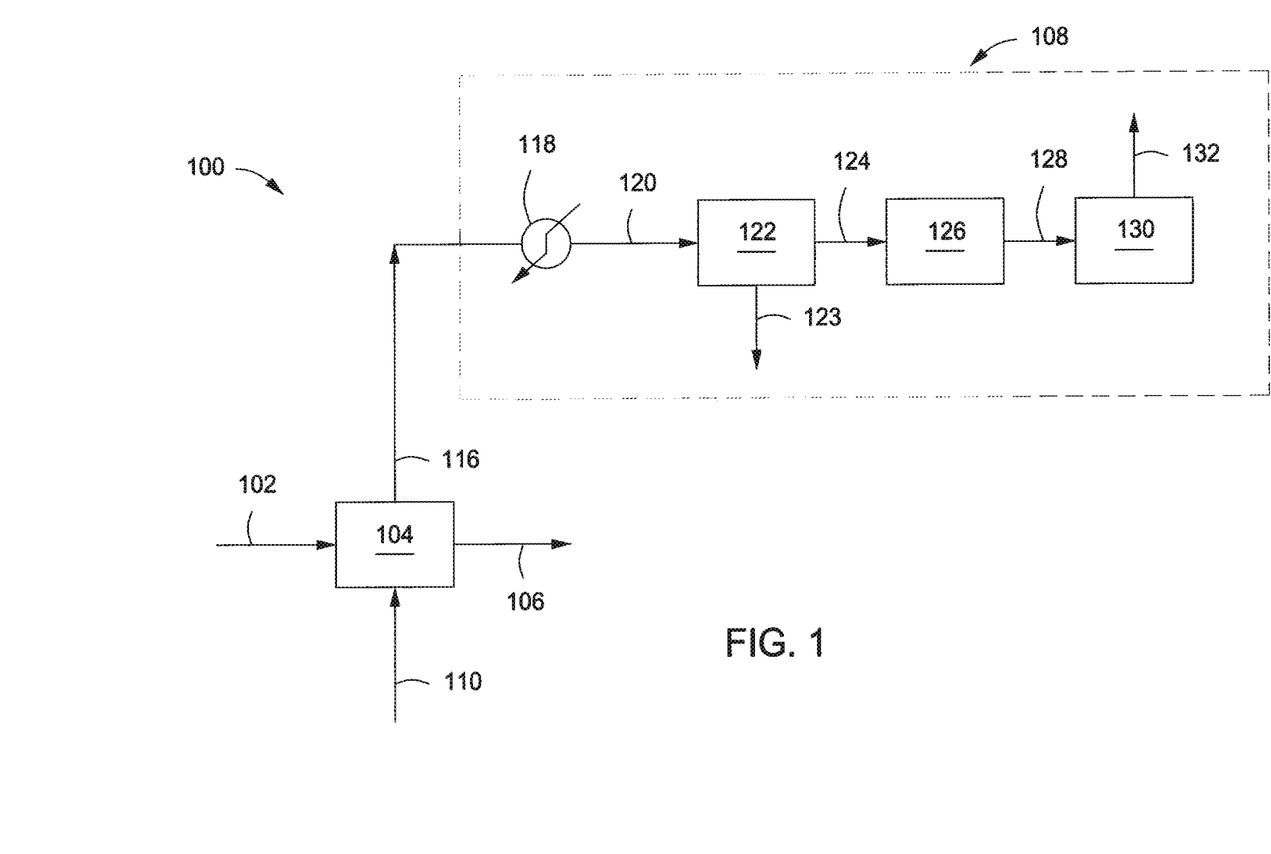
FIG. 1 depicts an illustrative cumene oxidation system with spent air treatment, according to one or more embodiments described herein.

FIG. 1 depicts an illustrative oxidation system 100 having a spent air purification unit 108, according to one or more embodiments. The oxidation system 100 can include one or more oxidation units 104 and one or more spent air purification units 108. The spent air purification unit can include one or more condensers 118, one or more spent air separation units 122, one or more adsorption and/or absorption units or simply "sorption units" 126, and one or more bioreactors 130. In a cumene oxidation process, fresh cumene (isopropylbenzene) containing feed and/or a recycled or spent cumene containing feed or simply "cumene feed" via line 110 can be introduced to the oxidation unit 104. An oxidant such as air or other molecular oxygen-containing gas via line 102 can be introduced to the oxidation unit 104. Each oxidation unit 104 can include any system or device adapted or configured to provide oxygen to the cumene feed introduced via line 110. For example, the oxidation unit 104 can include one or more bubble columns, e.g., a cascading arrangement of bubble columns (not shown). Residual oxygen or "spent air" via line 116 and an oxidized cumene product via line 106 can be recovered from the oxidation unit 104. The spent air via line 116 can be introduced to the spent air purification unit 108. For example, the spent air via line 116 can be introduced to the cooling unit or condenser 118 to produce a cooled spent air stream via line 120. The cooled spent air via line 120 can be introduced to one or more spent air separation units 122 to produce a separated spent air via line 124 and a liquid phase component containing water and/or organic compounds via line 123. The separated spent air in line 124 can have a liquid concentration, including liquid water and liquid organic compounds, less than a liquid concentration of the cooled spent air stream in line 120.

The separated spent air via line 124 can be introduced to the sorption unit 126 to remove or "scrub" the separated spent air of VOCs to produce a spent air having a reduced amount of VOCs. The spent air having the reduced amount of VOCs as compared to the separated spent air in line 124 can also be referred to as a "first purified air" or "scrubbed air" via line 128. The scrubbed air via line 128 can be introduced to the bioreactor or "biofilter" 130 to produce a treated, cleaned, or purified air via line 132. The treated air or "clean air" in line 132 can be essentially free or completely free of VOCs and NOx, which can eliminate the need for incineration. The clean air in line 132 can thus be emitted into the atmosphere without being subjected to incineration.

The clean air in line 123 can contain less than 50 ppmw, less than 35 ppmw, less than 20 ppmw, less than 10 ppmw, less than 5 ppmw, or less than 1 ppmw VOC. For example, the clean air in line 123 can contain from a low of about 0.0001 ppmw, about 0.0002 ppmw, about 0.005 ppmw, or about 0.01 ppmw to a high of about 0.05 ppmw, about 0.1 ppmw, about 0.5 ppmw, about 5 ppmw, about 10 ppmw, about 25 ppmw, about 40 ppmw, or about 50 ppmw VOCs. In an example, the clean air in line 123 can contain less than 1 ppmw, less than 0.5 ppmw, less than 0.1 ppmw, less than 0.01 ppmw, or less than 0.05 ppmw VOCs. In another example, the clean air in line 123 can be free of any VOC. The clean air in line 123 can contain less than 10 ppmw, less than 7 ppmw, less than 5 ppmw, less than 3 ppmw, less than 1 ppmw, less than 0.5 ppmw, less than 0.1 ppmw, less than 0.05 ppmw, or less than 0.01 ppmw NOx. For example, the clean air in line 123 can contain from a low of about 0.0001 ppmw, about 0.0002 ppmw, or about 0.001 ppmw to a high of about 0.005 ppmw, about 0.01 ppmw, about 0.1 ppmw, about 1 ppmw, or about 5 ppmw NOx. For example, the clean air in line 123 can contain less than 0.5 ppmw, less than 0.1 ppmw, less than 0.01 ppmw, or less than 0.05 ppmw NOx. In an example, the clean air in line 132 can contain essentially no NOx. For example, the clean air in line 132 can also be free of any NOx. As used herein, the term "essentially no" refers to amounts less than about 0.001 ppmw.

The cumene feed in line 110 can include at least 50 wt % cumene, at least 60 wt % cumene, at least 75 wt % cumene, or at least 90 wt % cumene. For example, the cumene feed in line 110 can include a low of about 60 wt %, about 70 wt %, or about 80 wt % to a high of about 90 wt %, about 95 wt %, or about 99 wt % cumene. In another example, the cumene feed in line 110 can include from about 85 wt % to about 99 wt % cumene, from about 90 wt % to about 99 wt % cumene, from about 95 wt % to about 99 wt % cumene. The cumene feed in line 110 can also include a low of about 0.01 wt %, about 0.1 wt %, about 1 wt %, or about 2 wt % to a high of about 3 wt %, about 4 wt %, or about 5 wt % cumene hydro-peroxide (CHP). The cumene feed in line 110 can include a low of about 0.01 wt %, about 0.1 wt %, about 0.15 wt %, or about 0.2 wt % to a high of about 0.3 wt %, about 0.4 wt %, or about 0.5 wt % dimethyl benzyl alcohol (DMBA). The cumene feed in line 110 can include a low of about 50 ppmw, about 100 ppmw, or about 150 ppmw to a high of about 200 ppmw, about 500 ppmw, or about 1,000 ppmw alpha-methyl styrene (AMS). The cumene feed in line 110 can be at a temperature from a low of about 30° C., about 40° C., or about 50° C. to a high of about 85° C., about 105° C., or about 120° C. The cumene feed in line 110 can be at a pressure from a low of about 50 kPag, about 100 kPag, about 200 kPag, or about 400 kPag to a high of about 600 kPag, about 700 kPag, about 800 kPag, or about 900 kPag.

The oxidant in line 102 can include, but is not limited to, air, oxygen, essentially oxygen. oxygen-enriched air, mixtures of oxygen and air, mixtures of air and/or oxygen with steam, mixtures of oxygen and one or more inert gases, for example, nitrogen, argon, ozone, hydrogen peroxide, or any combination thereof. For example, the oxidant in line 102 can contain about 20 vol % oxygen or more, about 30 vol % oxygen or more, about 40 vol % oxygen or more, about 50 vol % oxygen or more, about 60 vol % oxygen or more, about 65 vol % oxygen or more, about 70 vol % oxygen or more, about 75 vol % oxygen or more, about 80 vol % oxygen or more, about 85 vol % oxygen or more, about 90 vol % oxygen or more, about 95 vol % oxygen or more, or about 99 vol % oxygen or more. As used herein, the term "essentially oxygen" refers to an oxygen stream containing more than 50 vol % oxygen. As used herein, the phrase "oxygen-enriched air" or "oxygen enriched gas" refers to a gas mixture containing from about 21 vol % oxygen to about 50 vol % oxygen. Oxygen-enriched air and/or essentially oxygen can be obtained or produced, for example, from cryogenic distillation of air, pressure swing adsorption, membrane separation, or a combination thereof. The oxidant in line 102 can be at a temperature from a low of about 0° C., about 10° C., about 20° C., about 40° C., or about 60° C. to a high of about 70° C., about 80° C., about 90° C., about 100° C., or about 120° C. The oxidant in line 102 can have a pressure from a low of about 50 kPag, about 100 kPag, about 200 kPag, or about 400 kPag to a high of about 600 kPag, about 700 kPag, about 800 kPag, or about 900 kPag.

The oxidation unit 104 can include any system or device suitable to provide oxygen or other oxidant to the cumene feed introduced via line 110. For example, the oxidation unit 104 can include one or more (e g., a cascade) vertically oriented bubble columns (not shown). Further, the oxidant via line 102 can be air and can be added to the bottom of the bubble columns, such that oxygen from the air bubbles contacts the cumene. Operating conditions of the oxidation unit 104 can include a temperature from a low of about 45° C., about 65° C., or about 80° C. to a high of about 100° C., about 120° C., or about 150° C. and a pressure from a low of about 50 kPag, about 100 kPag, about 200 kPag, or about 400 kPag to a high of about 600 kPag, about 700 kPag, about 800 kPag, or about 900 kPag.

In one or more embodiments, the oxidation unit 104 can include one or more low pressure oxidizers (not shown) and/or one or more high pressure oxidizers (not shown). The low pressure oxidizer can be operated under a temperature from a low of about 45° C., about 65° C., or about 80° C. to a high of about 100° C., about 120° C., or about 150° C. and a pressure from a low of about 1 kPag, about 5 kPag, about 10 kPag, about 50 kPag, or about 100 kPag to a high of about 125 kPag, about 150 kPag, about 200 kPag, about 250 kPag, or about 300 kPag. The high pressure oxidizer can be operated under a temperature from a low of about 30° C., about 50° C., about 70° C., about 80° C., or about 90° C. to a high of about 100° C., about 110° C., about 120° C., about 130° C., or about 150° C. and a pressure from a low of about 100 kPag, about 150 kPag, about 200 kPag, about 250 kPag, or about 300 kPag to a high of about 350 kPag, about 400 kPag, about 500 kPag, about 750 kPag, or about 800 kPag. The number of low pressure reactors can be from 1 to 8, from 1 to 5, or from 2 to 4, and the number of high pressure reactors can be from 1 to 10, from 2 to 6, or from 3 to 5.

The cumene can have a residence time in the oxidation unit 104 from a low of about 1 hr, about 2 hr, about 4 hr, or about 6 hr to a high of about 10 hr, about 12 hr, about 15 hr, or about 20 hr. The oxidation reaction in the oxidation unit 104 can make, form, produce, or otherwise result in the production of methanol, which can be included in the oxidized product in line 106. One such reaction can convert cumene and oxygen to methyl-phenyl-ketone and methanol. Further, a portion of the methanol can be converted to methyl-hydrogen-peroxide (MHP) in the oxidation unit 104.

The oxidized product in line 106 can have a methanol concentration from a low of about 1 ppmw, about 5 ppmw, about 10 ppmw, about 50 ppmw, 100 ppmw, or about 500 ppmw to a high of about 0.1 wt %, about 0.5 wt %, about 1 wt %, about 2 wt %, about 4 wt %, or about 6 wt %. For example, the oxidized product in line 106 can have a methanol concentration from about 10 ppmw to about 5 wt %, from about 100 ppmw to about 2 wt %, or from about 500 ppmw to about 1 wt %. The oxidized product in line 106 can have a MHP concentration from a low of about 1 ppmw, about 5 ppmw, about 10 ppmw, about 50 ppmw, 100 ppmw, or about 500 ppmw to a high of about 0.1 wt %, about 0.5 wt %, about 1 wt %, about 2 wt %, about 4 wt %, or about 6 wt %. For example, the oxidized product in line 106 can have a MHP concentration from about 10 ppmw to about 5 wt %, from about 100 ppmw to about 2 wt %, or from about 500 ppmw to about 1 wt %. The oxidized product via line 106 can also include CHP. For example, the oxidized product via the line 106 can have a concentration of CHP from a low of about 10 wt %, about 15 wt %, about 20 wt %, or about 23 wt % to a high of about 25 wt %, about 27 wt %, about 30 wt %, about 35 wt %, or about 40 wt % CHP.

The spent air in line 116 can include oxygen in an amount from a low of about 0.5 wt %, about 1 wt %, or about 2 wt % to a high of about 6 wt %, about 8 wt %, or about 10 wt %. For example, the spent air in line 116 can have an oxygen concentration from about 1 wt % to about 8 wt %, about 2 wt % to about 6 wt %, or about 3 wt % to about 5 wt %. The spent air in line 116 can include nitrogen in an amount from a low of about 50 wt %, about 60 wt %, or about 70 wt % to a high of about 75 wt %, about 80 wt %, or about 85 wt %. For example, the spent air in line 116 can have a nitrogen concentration from about 68 wt % to about 85 wt %, about 71 wt % to about 83 wt %, or about 75 wt % to about 80 wt %. The spent air in line 116 can include water in an amount from a low of about 0.1 wt %, about 0.5 wt %, or about 1 wt % to a high of about 2 wt %, about 3.5 wt %, or about 5 wt %. For example, the spent air in line 116 can have a water concentration from about 0.5 wt % to about 4 wt %, about 2 wt % to about 5 wt %, or about 1 wt % to about 3.5 wt %.

The spent air in line 116 can include VOCs in any amount. For example, the spent air in line 116 can include VOCs, including non-aromatics, cumene, benzene, and/or toluene, in an amount from a low of about 1 wt %, about 5 wt %, about 8 wt %, about 10 wt %, or about 12 wt % to a high of about 20 wt %, about 25 wt %, about 30 wt %, about 35 wt %, or about 40 wt %. For example, the spent air in line 116 can have a non-aromatics, cumene, benzene, and toluene concentration from about 5 wt % to about 30 wt %, about 10 wt % to about 25 wt %, or about 15 wt % to about 20 wt %. The spent air in line 116 can include methanol, MHP, and formic acid in an amount from a low of about 1 ppmw, about 5 ppmw, about 10 ppmw, about 100 ppmw, or about 500 ppmw to a high of about 1,000 ppmw, about 2,000 ppmw, about 3,000 ppmw, about 5,000 ppmw, or about 1 wt %. For example. the spent air in line 116 can have a methanol, MHP, and formic acid concentration from about 10 ppmw to about 5,000 ppmw, about 200 ppmw to about 2,500 ppmw, or about 700 ppmw to about 3,500 ppmw.

The spent air in line 116 can have a temperature from a low of 50° C., about 60° C., about 65° C., or about 70° C. to a high of about 90° C., about 110° C., about 130° C., or about 150° C. The spent air in line 116 can be at a pressure from a low of about 5 kPag, about 10 kPag, about 25 kPag, about 100 kPag, or about 200 kPag to a high of about 500 kPag, about 600 kPag, about 750 kPag, about 900 kPag, or about 1,000 kPag.

The condenser 118 can include one or more heat exchangers of any type. For example, the condenser 118 can include one or more shell-and-tube heat exchangers, one or more cooling towers, and/or one or more refrigeration units. The condenser 118 can be operated at a temperature from a low of about −20° C., about −10° C., about −5° C., about −1° C., or about 0° C. to a high of about 2° C., about 4° C., about 8° C., about 10° C., or about 20° C. A cooled spent air in line 120 can be obtained or produced from the condenser 118. The cooled spent air in line 120 can have a temperature from a low of about −20° C., about −10° C., about −5° C., about −1° C., or about 0° C. to a high of about 2° C., about 4° C., about 8° C., about 10° C., or about 20° C.

The spent air separation unit 122 can include one or more separation drums or vessels in which a gaseous phase component and a liquid phase component are separated from the cooled spent air in line 120. In one or more embodiments, a gaseous phase component or separated spent air in line 124 and a liquid phase component, rich in cumene, water, and other organic compounds such as benzene, toluene, methanol, MHP, and formic acid, in line 123 are obtained or produced from the separation of the cooled spent air in the spent air separation unit 122. The liquid phase component in line 123 can have a total methanol/MHP/formic acid concentration from a low of about 0.01 wt %, about 0.05 wt %, about 0.1 wt %, about 0.3 wt %, or about 0.5 wt % to a high of about 1 wt %, about 2 wt %, about 4 wt %, about 6 wt %, or about 10 wt %. For example, the liquid phase component in line 123 can have a total methanol/MHP/formic acid concentration from about 0.01 wt % to about 10 wt %, about 0.5 wt % to about 5 wt %, or about 0.1 wt % to about 2 wt %. The liquid phase component in line 123 can have a water concentration from a low of about 1 wt %, about 5 wt %, about 8 wt %, or about 12 wt % to a high of about 15 wt %, about 20 wt %, about 30 wt % or about 40 wt %. For example, the methanol/water mixture in line 123 can have a water concentration from about 2 wt % to about 25 wt %, about 5 wt % to about 20 wt %, or about 8 wt % to about 15 wt %. The liquid phase component in line 123 can have a cumene concentration from a low of about 50 wt %, about 60 wt %, or about 80 wt % to a high of about 90 wt %, about 95 wt %, or about 99 wt %. For example, the liquid phase component in line 123 can have a cumene concentration from about 65 wt % to about 99 wt %, about 75 wt % to about 95 wt %, or about 84 wt % to about 92 wt %.

The separated spent air in line 124 can include molecular oxygen in an amount from a low of about 0.1 wt %, about 1 wt %, or about 2 wt % to a high of about 6 wt %, about 8 wt %, or about 12 wt %. For example, the separated spent air in line 124 can have a molecular oxygen concentration from about 0.5 wt % to about 10 wt %, about 1 wt % to about 8 wt %, or about 3 wt % to about 7 wt %. The separated spent air in line 124 can include nitrogen in an amount from a low of about 60 wt %, about 70 wt %, or about 80 wt % to a high of about 90 wt %, about 95 wt %, or about 99 wt %. For example, the separated spent air in line 124 can have a nitrogen concentration from about 75 wt % to about 99 wt %, about 85 wt % to about 95 wt %, or about 92 wt % to about 98 wt %.

The separated spent air in line 124 can include VOCs, such as a combination or mixture of non-aromatics, cumene, benzene, and toluene, in an amount from a low of about 100 ppmw, about 500 ppmw, about 750 ppmw, or about 1,000 ppmw to a high of about 0.2 wt %, about 0.6 wt %, about 1 wt %, or about 5 wt %. For example, the separated spent air in line 124 can have a non-aromatics/cumene/benzene/toluene concentration from about 100 ppmw to about 1 wt %, about 500 ppmw to about 0.6 wt %, or about 1000 ppmw to about 0.2 wt %.

The separated spent air in line 124 can include methanol and formic acid in an amount from a low of about 1 ppmw, about 5 ppmw, or about 10 ppmw to a high of about 100 ppmw, about 500 ppmw, or about 1000 ppmw. For example, the separated spent air in line 124 can have a methanol/formic acid concentration from about 1 ppmw to about 5 ppmw, about 10 ppmw to about 100 ppmw, or about 500 ppmw to about 1000 ppmw. The separated spent air in line 124 can have a temperature from a low of about $-20°$ C. about $-10°$ C., about $-5°$ C., about $-1°$ C., or about $0°$ C. to a high of about $5°$ C., about $10°$ C., about $15°$ C., about $20°$ C., or about $30°$ C. The separated spent air in line 124 can be at a pressure from a low of about 10 kPag, about 50 kPag, about 100 kPag, or about 200 kPag to a high of about 500 kPag, about 700 kPag, about 1,000 kPag, about 1,500 kPag, or about 2,000 kPag.

One element of the invention of the application is that no supplemental water is introduced into the spent air prior to it being cooled. In one embodiment of the method of the application, the spent air is cooled using a condenser. For example, in one embodiment illustrated by FIG. 1, no supplemental water at any material concentration is introduced upstream of the condenser 118. Any apparatus/unit useful for cooling spent air may be used in this limitation of the claims. In some embodiments, the sorption unit 126 itself can be a cooling unit. In this embodiment, no supplemental water at a material concentration is introduced upstream from the sorption unit 126.

For the purposes of this application, the term material concentration means concentrations of 0.00005 gallons per standard cubic foot of spent air or higher. The introduction of 0.00005 gallons per standard cubic foot of spent air or higher would have a material impact upon the spent air if introduced upstream from the condensers of the system of the application.

The separated spent air in line 124 can be introduced to the sorption unit 126. The sorption unit 126 can include any system, device, or combination of systems and/or devices capable of separating at least a portion of the VOCs, including the non-aromatics, benzene, toluene, cumene, methanol, and formic acid, contained in the separated spent air introduced thereto via line 124. For example, the sorption unit 126 can include one or more absorption unit or solvent absorption unit 126 for contacting the separated spent air in line 124 with a liquid solvent.

The liquid solvent can include diethylene glycol (DEG), triethylene glycol (TEG), acetic acid, acetic anhydride, dimethyl sulfoxide, chlorobenzene, deuterium oxide, ethylene glycol, diisopropylbenzene (DIPB), propylene carbonate, formic acid, 1,2-dichloroethane, glycerin, 1,2-dichlorobenzene, methylene chloride, and the like. For example, the liquid solvent can include DEG, TEG, DIPB, or any combination or mixture thereof. In an example, the liquid solvent can include DEG. The DEG liquid solvent can be a solvent and water mixture having a solvent concentration from a low of about 40 wt %, about 60 wt %, or about 75 wt % to a high of about 85 wt %, about 95 wt %, or about 99 wt % based on the weight of the mixture. For example, the liquid solvent can have a DEG concentration from a low of about 40 wt %, about 60 wt %, or about 75 wt % to a high of about 85 wt %, about 95 wt %, or about 99 wt % and a water concentration from a low of about 1 wt %, about 5 wt %, or about 15 wt % to a high of about 25 wt %, about 40 wt %, or about 60 wt % based on the weight of the liquid solvent.

The liquid solvent can be introduced to the sorption unit 126 at a mass flow rate ratio of solvent (in kilograms) to separated spent air (in kilograms) from a low of about 1:1, about 3:1, or about 5:1 to a high of about 10:1, about 15:1, or about 20:1. The solvent can be introduced to the sorption unit 126 at a temperature from a low of about $-50°$ C., about $-20°$ C., about $-10°$ C., about $-5°$ C., about $-1°$ C., or about $1°$ C. to a high of about $4°$ C., about $6°$ C., about $8°$ C., about $15°$ C., about $30°$ C., or about $50°$ C. and a pressure from a low of about 10 kPag, about 50 kPag, about 100 kPag, about 150 kPag, or about 250 kPag to a high of about 500 kPag, about 600 kPag, about 700 kPag, about 1,000 kPag, or about 1,500 kPag.

The sorption unit 126 can include one or more vessels for contacting the separated spent air with one or more liquid solvents. For example, the sorption unit 126 can be or include one or more columns (not shown) for gas-liquid contacting. The column can be empty, partially filled, or completely filled with one or more materials to improve mass transfer and/or separation of the VOCs from the separated spent air. For example, the fill material can include, but is not limited to, structured materials, random packed materials, trays, or any combination thereof. Two or more types of fill material can be disposed within the column. For example, the column can contain random dumped packing and one or more trays.

As used herein, the term "trays" can include, but is not limited to, one or more types of trays that can improve the contact between gas and/or liquid phases within the column of the absorption unit 126. Illustrative trays can include, but are not limited to perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof. As used herein, the term "packing material" can include, but is not limited to one or more types of structured and/or random shaped material disposed within the column of the absorption unit 126, The packing material can increase the effective surface area within the column of the absorption unit 126, which can improve the mass transfer between liquid and/or gas phases within the column, The packing material can be made of any suitable material, for example metals, non-metals, polymers, ceramics, glasses, or any combination thereof. Illustrative examples of commercially available random packing material can include, but are not limited to, IMTP®, INTALOX® ULTRA™, Raschig rings, A-Pak Rings, Saddle Rings, Nutter Rings™, I-Rings™, C-Rings™, P-Rings™, R-Rings™, or any combination thereof. Illustrative examples of commercially available structured packing can include, but are not limited to, structured packing, corrugated sheets, crimped sheets, gauzes, grids, wire mesh, monolith honeycomb structures, or any combination thereof. For example, suitable structured packing can include but not limited to FLEXIPAC®, FLEXIPAC®, HC®,INTERLOX®, Montz-Pak, Mellapak™, MellapakPlus™, GT-PAK™, GT-OPTIM™ PAK, etc.

The liquid solvent can be introduced into an upper portion of the column of the absorption unit 126 and the separated spent air can be introduced into the lower portion of the column. The separated spent air can rise in the column and come into contact with the falling liquid solvent. The falling liquid solvent can absorb VOCs in the separated spent air. For example, the liquid solvent can absorb non-aromatics, cumene, benzene, toluene, and any combination or mixture thereof in an amount from a low of about 10 ppmw, about 100 ppmw, about 500 ppmw, or about 1,000 ppmw to a high of about 0.2 wt %, about 0.6 wt %, about 1 wt %, about 5 wt %, or about 10 wt % based on the total weight of non-aromatics, cumene, benzene, and/or toluene in the separated spent air introduced to the column of the absorption unit 126. The liquid solvent can absorb methanol and/or formic acid in an amount from a low of about 1 ppmw, about 5 ppmw, about 10 ppmw, or about 50 ppmw to a high of about 100 ppmw, about 500 ppmw, 1,000 ppmw, or about 2,500 ppmw based on the total weight of methanol and/or formic acid in the separated spent air introduced to the column of the absorption unit 126. The column of the absorption unit 126 can be operated at a temperature from a low of about −50° C., about −20° C., about −10° C., about −5° C., or about 0° C. to a high of about 6° C., about 10° C., about 20° C., about 35° C., or about 50° C. and a pressure from a low of about 10 kPag, about 50 kPag, about 100 kPag, or about 200 kPag to a high of about 500 kPag, about 600 kPag, about 700 kPag, or about 1,500 kPag.

The sorption unit 126 can include multiple zones where the liquid solvent can be introduced to each zone separately, at different temperatures. For example, the sorption unit 126 can include a vertically oriented column (not shown) having an upper zone (not shown) located at a top end (not shown) of the column and a lower zone (not shown) located at a bottom end (not shown) of the column. In an example, the liquid solvent can be introduced separately to the upper zone and the lower zone, where the solvent introduced to the upper zone can be at a lower temperature than the solvent introduced to the lower zone. The number of zones in the absorption unit 126 can be optimized depending on the type of solvent used, the concentration of the solvent, the operating pressure of the absorption unit, and the temperature of each zone.

The scrubbed air in line 128 can include oxygen in an amount from a low of about 1 wt %, about 4 wt %, or about 6 wt % to a high of about 8 wt %, about 12 wt %, or about 20 wt %. For example, the scrubbed air in line 128 can have an oxygen concentration from about 2 wt % to about 15 wt %, about 3 wt % to about 12 wt %, or about 1 wt % to about 8 wt %. The scrubbed air in line 128 can include nitrogen in an amount from a low of about 60 wt %, about 70 wt %, or about 80 wt % to a high of about 90 wt %, about 95 wt %, or about 99 wt %. For example, the scrubbed air in line 128 can have a nitrogen concentration from about 75 wt % to about 99 wt %, about 85 wt % to about 95 wt %, or about 92 wt % to about 98 wt %.

The scrubbed air in line 128 can include non-aromatics, cumene, benzene, and/or toluene in an amount from a low of about 10 ppmw, about 50 ppmw, about 100 ppmw, or about 200 ppmw to a high of about 500 ppmw, about 700 ppmw, about 1,000 ppmw, or about 2,500 ppmw. For example, the scrubbed air in line 128 can have a non-aromatics/cumene/benzene/toluene concentration from about 5 ppmw to about 1,500 ppmw, about 75 ppmw to about 750 ppmw, or about 100 ppmw to about 500 ppmw. The scrubbed air in line 128 can include methanol and/or formic acid in an amount from a low of about 1 ppmw, about 5 ppmw, or about 10 ppmw to a high of about 100 ppmw, about 250 ppmw, or about 500 ppmw. For example, the scrubbed air in line 128 can have a methanol/formic acid concentration from about 1 ppmw to about 500 ppmw, about 5 ppmw to about 250 ppmw, or about 10 ppmw to about 100 ppmw.

The scrubbed air in line 128 can have a temperature from a low of about −30° C., about −20° C., about −10° C., about −5° C., or about 0° C. to a high of about 2° C., about 8° C., about 12° C., about 20° C., or about 30° C. The scrubbed air in line 128 can be at a pressure from a low of about 10 kPag, about 50 kPag, about 100 kPag, or about 200 kPag to a high of about 500 kPag, about 600 kPag, about 700 kPag, or about 1,500 kPag.

In one or more embodiments, in addition to or in lieu of the liquid sorbent, the sorption unit 126 can include a solid adsorbent. In an example, the solid adsorbent can be or include activated carbon. The activated carbon can be or include powdered activated carbon, granular activated carbon, extruded activated carbon, bead activated carbon, impregnated activated carbon, polymer activated carbon, or any other composition containing activated carbon. In one or more embodiments, the sorption unit 126 can include one or more activated carbon beds in a parallel or series arrangement. The loading of the VOCs on the activated carbon beds in VOCs (in kilograms) to carbon (in kilograms) can be from a low of about 1:10, about 2:10, or about 3:10 to a high of about 5:10, about 6:10, or about 7:10. The sorption unit 126 can have any number of activated carbon beds. For example, the sorption unit 126 can have from a low of 1, 2, or 3 to a high of 5, 8, or 10 carbon beds. In another example, the sorption unit 126 can include from 1 to 6 carbon beds or from 2 to 4 carbon beds.

In one or more embodiments, the solid adsorbent can include molecular sieves, zeolitic materials, activated alumina, silica gels, alumina-silica gels, naturally occurring clays. In one or more embodiments, the sorption unit 126 can include one or more zeolite beds. The loading of the VOCs on the zeolite beds in VOCs (in kilograms) to zeolite (in kilograms) can be from a low of about 1:10, about 2:10, or about 3:10 to a high of about 5:10, about 6:10, or about 7:10. The sorption unit 126 can have any number of zeolite beds. The sorption unit 126 can have from a low of 1, 2, or 3 to a high of 5, 8, or 10 zeolite beds. In another example, the sorption unit 126 can include from 1 to 6 zeolite beds or from 2 to 4 zeolite beds.

The solid adsorbent can be operated at a temperature from a low of about −20° C., about 0° C., about 10° C., about 20° C., or about 30° C. to a high of about 40° C., about 50° C., about 60° C., about 80° C., or about 100° C. and a pressure from a low of about 1 kPag, about 5 kPag, about 10 kPag, about 20 kPag, or about 30 kPag to a high of about 40 kPag, about 50 kPag, about 60 kPag, about 80 kPag, or about 100 kPag.

The scrubbed air in line 128, when the sorption unit 126 includes a solid adsorbent, can include oxygen in an amount from a low of about 1 wt %, about 4 wt %, or about 6 wt % to a high of about 8 wt %, about 12 wt %, or about 20 wt %. For example, the scrubbed air in line 128, when the sorption unit 126 includes a solid adsorbent, can have an oxygen concentration from about 2 wt % to about 15 wt %, about 3 wt % to about 12 wt %, or about 1 wt % to about 8 wt %. The scrubbed air in line 128, when the sorption unit 126 includes a solid adsorbent, can include nitrogen in an amount from a low of about 60 wt %, about 70 wt %, or about 80 wt % to a high of about 90 wt %, about 95 wt %, or about 99 wt %. For example, the scrubbed air in line 128, when the sorption unit 126 includes a solid adsorbent, can have a nitrogen concentration from about 75 wt % to about 99 wt %, about 85 wt % to about 95 wt %, or about 92 wt % to about 98 wt %.

The scrubbed air in line 128, when the sorption unit 126 includes a solid adsorbent, can include non-aromatics, cumene, benzene, and/or toluene in an amount from a low of about 10 ppmw, about 25 ppmw, or about 40 ppmw to a high of about 50 ppmw, about 75 ppmw, or about 100 ppmw. For example, the scrubbed air in line 128 can have a non-aromatics/cumene/benzene/toluene concentration from about 10 ppmw to about 100 ppmw, about 25 ppmw to about 75 ppmw, or about 40 ppmw to about 60 ppmw. The scrubbed air in line 128, when the sorption unit 126 includes a solid adsorbent, can include methanol and/or formic acid in an amount from a low of about 1 ppmw, about 3 ppmw, or about 5 ppmw to a high of about 10 ppmw, about 15 ppmw, or about 30 ppmw. For example, the scrubbed air in line 128 can have a methanol/formic acid concentration from about 1 ppmw to about 30 ppmw, about 3 ppmw to about 15 ppmw, or about 5 ppmw to about 10 ppmw.

When the sorption unit 126 includes a solid adsorbent, the scrubbed air in line 128 can have a temperature from a low of about −20° C., about −10° C., about −5° C., about 0° C., or about 10° C. to a high of about 20° C., about 25° C., about 30° C., about 40° C., or about 50° C. The scrubbed air in line 128, when the sorption unit 126 includes a solid adsorbent, can be at a pressure from a low of about 1 kPag, about 5 kPag, about 10 kPag, about 25 kPag, or about 40 kPag to a high of about 50 kPag, about 75 kPag, about 100 kPag, about 150 kPag, or about 500 kPag.

In one or more embodiments, the sorption unit 126 can include any combination of solvent absorption and solid adsorbent units containing active carbon and/or zeolitic materials. These units can be arranged in series or parallel configuration. In a series configuration, for example, the cooled spent air via line 124 can be introduced first to a solvent absorption unit followed by one or more solid adsorbent units containing active carbon and/or zeolitic materials.

The scrubbed air in line 128 can be introduced to the bioreactor 130. The bioreactor 130 can include any system, device, or combination of systems and/or devices containing a biological material and capable of separating at least a portion of the remaining VOCs contained in the scrubbed air introduced thereto via line 128. For example, the bioreactor 130 can include one or more biofilters each containing biological material. As used herein, the term "biological material" refers to any material derived, produced, or obtained from a living organism. The bioreactor 130 can include one or more columns, one or more vessels, and/or any other container containing biological material. The bioreactor 130 can direct flow of the scrubbed air in line 128 through a biological material of the bioreactor 130 to obtain or produce a final discharge or clean air in line 132.

The biological material can include, but is not limited to, activated sludge, waste water, algae, microbes or microbial organisms, plant mulch, soil, bark, wood chips, sawdust, grass clippings, peat, manure, compost, and the like. The bioreactor 130 can include one or more layers of biological material. Each layer of biological material can be the same or different. The bioreactor 130 can have from a low of 1, 2, or 3 to a high of 5, 7, or 10 layers of biological material. In an example, two or more layers of biological material can be separated by a void or space, inert material, packing, activated carbon, or the like. In an example, two or more layers of biological material can be disposed on top of one another. In one or more embodiments, the bioreactor 130 can include from 1 to 6 layers of biological material or from 2 to 4 layers of biological material.

The biological material can remove at least a portion of VOCs, including non-aromatics, cumene, benzene, toluene, methanol, and formic acid, present in the scrubbed air. For example, the biological material can remove at least about 50 wt %, at least about 75 wt %, at least about 85 wt %, at least about 90 wt %, at least about 95 wt %, at least about 99 wt %, at least about 99.99 wt %, or 100% of the non-aromatics, cumene, benzene, and/or toluene present in the scrubbed air introduced to the biological reactor 130. The biological material can remove at least about 50 wt %, at least about 75 wt %, at least about 85 wt %, at least about 90 wt %, at least about 95 wt %, at least about 99 wt %, at least about 99.99 wt %, or 100% of the methanol and/or formic acid in the scrubbed air introduced to the biological reactor 130. The biological reactor can be operated under a temperature from a low of about −30° C., about −15° C., about 0° C., about 10° C., or about 20° C. to a high of about 25° C., about 35° C., about 45° C., about 60° C., or about 75° C. and a pressure from a low of about 1 kPag, about 3 kPag, or about 5 kPag, to a high of about 7 kPag, about 10 kPag, about 12 kPag, about 15 kPag, or about 20 kPag. In one or more embodiments, the biological reactor can operate without an external heat source and without downstream incineration. For example, the spent air via line 116 from the oxidation unit 104 can be purified and subsequently discharged to the atmosphere without entering or being introduced to an incinerator.

Although not shown in FIG. 1, at least a portion of the waste water can be introduced to the bioreactor 130. In an example, the biological material can be replenished via make-up, addition, or circulation of biological sludge from an activated sludge unit. The activated sludge unit can also receive waste water produced from the cumene oxidation process disclosed herein.

The clean air in line 132 can include oxygen in an amount from a low of about 1 wt %, about 4 wt %, or about 6 wt % to a high of about 8 wt %, about 12 wt %, or about 20 wt %. For example, the clean air in line 132 can have an oxygen concentration from about 2 wt % to about 15 wt %, about 3 wt % to about 12 wt %, or about 1 wt % to about 8 wt %. The clean air in line 132 can include nitrogen in an amount from a low of about 60 wt %, about 70 wt %, or about 80 wt % to a high of about 90 wt %, about 95 wt %, or about 99 wt %. For example, the clean air in line 132 can have a nitrogen concentration from about 75 wt % to about 99 wt %, about 85 wt % to about 95 wt %, or about 92 wt % to about 98 wt %.

The clean air in line 132 can include non-aromatics, cumene, benzene, and/or toluene in an amount from a low of 0 ppmw, about 0.0001 ppmw, or about 0.001 ppmw to a high of about 0.01 ppmw, about 0.05 ppmw, or about 0.1 ppmw. For example, the clean air in line 132 can have a non-aromatics/cumene/benzene/toluene concentration from 0.0001 ppmw to about 0.075 ppmw, about 0.0005 ppmw to about 0.04 ppmw, or about 0.001 ppmw to about 0.02 ppmw.

The clean air in line 132 can include methanol and/or formic acid in an amount from a low of 0 ppmw, about 0.0001 ppmw, or about 0.001 ppmw to a high of about 0.01 ppmw, about 0.05 ppmw, or about 0.1 ppmw. For example, the clean air in line 132 can have a methanol/formic acid concentration from 0 ppmw to about 0.075 ppmw, about 0.0001 ppmw to about 0.04 ppmw, or about 0.001 ppmw to about 0.02 ppmw. The clean air in line 132 can contain essentially no NOx, non-aromatics/cumene/benzene/toluene, and/or methanol/formic acid. In a further example, the clean air in line 132 can contain essentially no non-aromatics/cumene/benzene/toluene, and; or methanol/formic acid and contains no NOx. The clean air in line 132 can have a temperature from a low of about −10° C., about 0° C. about 10° C., about 15° C., or about 20° C. to a high of about 35° C., about 40° C., or about 45° C., about 50° C., or about 55° C. The clean air in line 132 can be introduced to the atmosphere.

Figure 2:
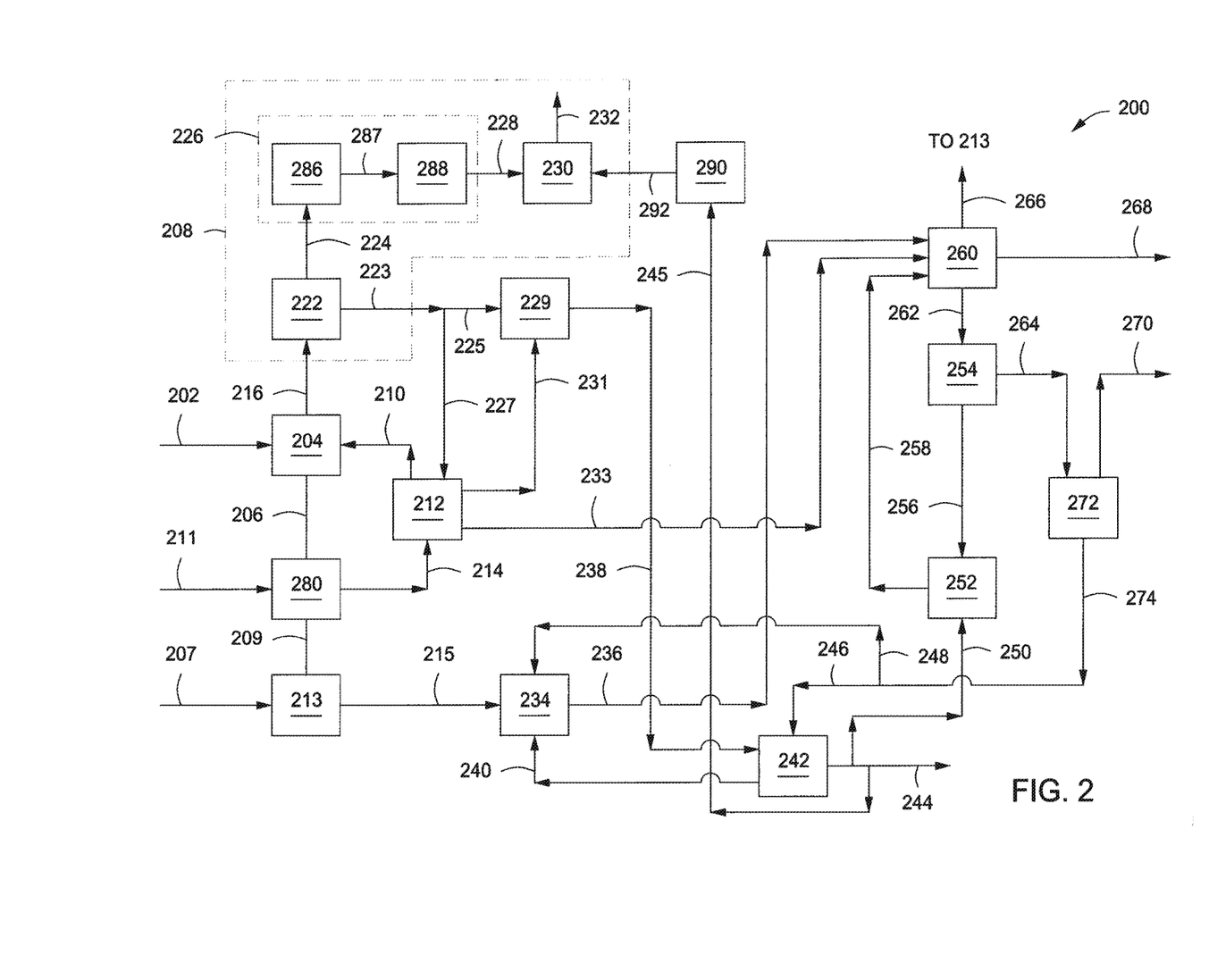
FIG. 2 depicts an illustrative system for producing acetone with spent air treatment, according to one or more embodiments described herein.

FIG. 2 depicts an illustrative system 200 for producing phenol and acetone, according to one or more embodiments. The system 200 can include one or more oxidation units 204 configured to receive cumene via line 210 and an oxidant via line 202 and to produce an oxidized product via line 206. The oxidation unit 204 can be any system or device suitable to provide an oxidant, e.g., oxygen, to the cumene introduced via line 210. For example, the oxidation unit 204 can include one or more vertically oriented bubble columns (not shown). Further, the oxidant via line 202 can be air and can be added to the bottom of the bubble columns, such that oxygen transfers from the air bubbles into the cumene. Spent air via line 216 and the oxidized cumene product via line 206 can be obtained or produced from the oxidation unit 204. The spent air in line 216 can be introduced to one or more spent air purification units 208. The spent air purification unit 208 can include one or more spent air separation units 222 to obtain or produce a separated spent air stream in line 224 from the spent air in line 216. The separated spent air in line 224 can be introduced to one or more sorption units 226 to produce scrubbed air via line 228. The scrubbed air via line 228 can be introduced to one or more bioreactors or biofilters 230 to produce a clean air via line 232.

The oxidation reaction can produce methanol, which can be included in the oxidized product in line 206. One such reaction can convert cumene and oxygen to methyl-phenyl-ketone and methanol. Further, a portion of the methanol can be converted to methyl-hydrogen-peroxide (MHP). The cumene in line 210 can be recycled to the oxidation unit 204 from a cumene wash unit 212. The oxidized product via line 206 can also include CHP.

The oxidized product via line 206 can be introduced to one or more concentration units 280. The concentration unit 280 can include one or more vacuum distillation columns, heat exchangers, reflux drums, etc. In such vacuum distillation columns, cumene can be separated at temperatures below about 100° C., for example. The concentration unit 280 can also receive cumene via a line 211, which can be introduced as reflux to one or more of the vacuum distillation columns to improve yield performance. The concentration unit 280 can produce a crude concentrated CHP product via line 209 and cumene via line 214.

The crude concentrated CHP product via line 209 can be introduced to one or more cleavage units 213. One or more acids via line 207 can also be introduced to the cleavage unit 213. Suitable acids that can be introduced via line 207 to the cleavage unit 213 can include, but are not limited to, sulphuric acid. The cleavage unit 213 can include a continuously-stirred tank reactor (not shown) and/or a circulation loop (not shown) with one or more heat exchangers included therein. The crude concentrated CHP product can be introduced to the circulation loop to produce acetone and phenol. Further, the cleavage reaction can be exothermic, thus the heat exchangers can be provided with cooling water or another heat exchange fluid to control the temperature of the concentrated feed in the cleavage unit 213. In the cleavage unit 213, DMBA can be partially dehydrated to AMS, which can react in consecutive reactions with phenol to form cumylphenols. AMS can also form high-boiling point dimers in the cleavage unit 213. DMBA reacts with CHP to form dicumyl peroxide (DCP) and water. Additional byproducts can also be produced, such as hydroxyacetone, 2-methylbenzofurane (2MBF), and diacetone alcohol. These products can be fed to a plug-flow reactor (not shown), for example, at temperatures of about 100° C. or more. In the plug flow reactor, DCP can revert to CHP and DMBA, CHP can be cleaved to phenol and acetone, and DMBA can be dehydrated to AMS and water. At least a portion of these products can be discharged from the cleavage unit 213 as a crude product feed via line 215. One example of a cleavage unit can be as discussed and described in U.S. Pat. No. 5,371,305.

The crude cleavage product containing phenol and acetone can be further purified into phenol and acetone products in subsequent processing units. For example, the crude product via line 215 can be introduced to one or more neutralization units 234. The neutralization unit 234 can also receive a salt solution via line 128. For example, the salt solution in line 240 can be sodium phenate. The salt solution can reduce or quench any continuing cleavage reactions in the crude product feed. Accordingly, the neutralization unit 234 can produce a neutralized crude product via line 236.

The neutralized crude product via line 236, which can include acetone and phenol, can be introduced to one or more acetone fractionation systems 260. The acetone fractionation system 260 can be or include one or more distillation columns (FIG. 2). In the system 260, an acetone product can be recovered via lines 266 and 268. Although not shown, the acetone product via line 266 can be directed back or recycled to the cleavage unit 213. For example, the acetone product via line 266 can include sulfuric acid and can thus mix with or provide the acid received by the cleavage unit 213. The addition of acetone to the cleavage unit 213 can raise or increase the AMS yield contained in the crude product via line 215 recovered therefrom. The acetone product via line 268 can be directed to a storage container, or can be otherwise stored, transported, or processed for subsequent use.

The acetone product via line 268 can have a methanol concentration from about 1 ppmw to about 140 ppmw. For example, the acetone product via line 268 can have a methanol concentration from a low of about 10 ppmw, about 20 ppmw, about 30 ppmw, about 40 ppmw, about 50 ppmw, about 55 ppmw, about 60 ppmw, about 65 ppmw, or about 70 ppmw to a high of about 80 ppmw, about 85 ppmw, about 90 ppmw, about 95 ppmw, about 100 ppmw, about 110 ppmw, or about 120 ppmw. In another example, the methanol concentration in the acetone product via line 268 can be about 65 ppmw, about 70 ppmw, about 75 ppmw, about 80 ppmw, or about 85 ppmw. In another example, the methanol concentration in the acetone produce in via line 268 can be less than about 85 ppmw, less than about 80 ppmw, less than about 75 ppmw, less than about 70 ppmw, less than about 65 ppmw, less than about 60 ppmw, less than about 55 ppmw, or less than about 50 ppmw. An acetone bottoms product via line 262 can be recovered from the acetone fractionation system 260 and can be introduced to one or more acetone bottoms separators 254. The acetone bottoms separator 254 can be a distillation column, vacuum distillation column, adsorption unit, cyclonic separator, a combination thereof, or any other separation unit. The acetone bottoms separator 254 can separate the acetone bottoms product into a phenate product via line 264 and a crude AMS product via line 256. The crude AMS product via line 256 can be washed of residual caustic in one or more AMS wash units 252 to produce a washed AMS via line 258. The washed AMS via line 258 can then be recycled back to the acetone fractionation system 260.

The phenate product via line 264 can be introduced to one or more methanol removal columns 272. The methanol removal column 272 can include one or more distillation columns, reflux drums, heat exchangers, etc. to remove at least a portion of the methanol from the phenate in line 264. For example, a distillation column of the methanol removal column 272 can be operated above the boiling temperature and pressure of methanol to remove methanol via line 270 from the phenate product in line 264. The methanol, along with phenol, acetone, and/or other hydrocarbons, can be recovered as a methanol product via line 270. A methanol-depleted product can be removed via line 274 and/or introduced via line 248 to the neutralization unit 234 and introduced via line 246 to one or more dephenolation units 242. The methanol-depleted product via line 274 can have a methanol concentration of less than about 100 ppmw, less than about 50 ppmw, less than about 25 ppmw, less than about 10 ppmw, less than about 5 ppmw, or less than about 1 ppmw.

The methanol-depleted product via line 246 can be received in a dephenolation unit 304 to aid in the dephenolation process therein. The dephenolation unit 242 can also receive a decomposed MHP via line 238 from one or more MHP decomposer units 229. The dephenolation unit 242 can separate at least a portion of any phenol present in one or more feeds introduced thereto, and can recover the phenol as sodium phenate via line 240. The sodium phenate via line 240 can then be introduced to the neutralization unit 234, as discussed and described above. The dephenolation unit 242 can also produce a waste water via line 305. At least a portion of the waste water via line 244 can be recycled via line 250 to the AMS wash 252, and/or at least a portion of the waste water can be discharged for further processing, disposal, etc. The waste water via line 244 can have a methanol concentration from a low of about 0.10 wt %, about 0.20 wt %, about 0.25 wt %, about 0.30 wt %, or about 0.34 wt % to a high of about 0.36 wt %, about 0.40 wt %, about 0.45 wt %, about 0.50 wt %, or about 0.60 wt %. An example of a dephenolation unit is discussed and described in U.S. Pat. No. 6,824,687.

A MHP decomposer unit 229 can receive a spent caustic via line 231 from one or more cumene wash units 212 and aqueous stream containing methanol and MHP via lines 223, 225 from one or more spent air separation units 222. The MHP decomposer unit 229 can mix, blend, or otherwise contact a methanol, water, MHP, and formic acid mixture via line 225 with the spent caustic via line 231, to produce at least methanol. hydrogen, formic acid, formaldehyde, and water, which can form the decomposed MHP via line 238.

The cumene wash unit 212 can receive cumene via line 214 from the concentration unit 280 and/or cumene via line 227 from the spent air separation units 222. The cumene wash unit 212 can remove at least a portion of any organic acids, such as formic acid, formed in the oxidation unit 204 to prevent corrosion on downstream sections. The cumene wash unit 212 can include one or more cumene extraction columns, where cumene hydro-peroxide (CHP) can be extracted using the cumene via line 214. The cumene wash unit 212 can also receive waste water (not shown) to remove residual caustic from the cumene 214. One example of a cumene wash unit is discussed and described in U.S. Pat. No. 5,220,103.

The cumene wash unit 212 can provide the cumene via line 210, which can be introduced to the oxidation unit 204, and spent caustic via line 231 to the MHP decomposer unit 229. The cumene wash unit 212 can also provide waste water via line 233 to the acetone fractionation system 260.

The waste water via line 233 can serve to provide additional dilution for a caustic soda injection into the acetone fractionation system 260 and/or can be introduced into the acetone fractionation system 260 to increase methanol concentration in the bottoms product via line 262.

The spent air separation unit 222 can receive a spent air via line 216 from the oxidation unit 204. The spent air separation unit 222 can include one or more coolers, gas-liquid separators, hydrocyclonic separators, and/or another structure configured to remove at least a portion of any hydrocarbons from the spent air via line 216. For example, the spent air separation unit 222 can remove cumene and/or other hydrocarbons and recover the cumene via line 227 for introduction to the cumene wash unit 212, and an aqueous stream via line 225 to another processing unit (not shown). The spent air separation unit 222 can also produce a separated separated spent air via line 224.

The separated spent air via line 224 can include VOCs, such as a combination or mixture of non-aromatics, cumene, benzene, and toluene, in an amount from a low of about 100 ppmw, about 500 ppmw, about 750 ppmw, or about 1,000 ppmw to a high of about 0.2 wt %, about 0.6 wt %, about 1 wt %, or about 5 wt %. For example, the separated spent air in line 224 can have a non-aromatics/cumene/benzene/toluene concentration from about 100 ppmw to about 1 wt %, about 500 ppmw to about 0.6 wt %, or about 1000 ppmw to about 0.2 wt %. The separated spent air in line 224 can also include methanol and formic acid in an amount from a low of about 1 ppmw, about 5 ppmw, or about 10 ppmw to a high of about 100 ppmw, about 500 ppmw, or about 1000 ppmw. For example, the separated spent air in line 224 can have a methanol/formic acid concentration from about 1 ppmw to about 5 ppmw, about 10 ppmw to about 100 ppmw, or about 500 ppmw to about 1000 ppmw.

The separated spent air in line 224 can be introduced to the sorption unit 226. The sorption unit 226 can include any system, device, or combination of systems and/or devices capable of separating at least a portion of VOCs contained in the separated spent air introduced thereto via line 224. The sorption unit 226 can include one or more solvent adsorption units 286 and/or one or more solid adsorbent units 288 arranged in a series or parallel configuration. In a series configuration as shown in FIG. 2, for example, the cooled spent air via line 224 can be introduced first to the solvent absorption unit 286 followed by the solid adsorbent unit 288 containing active carbon and/or zeolitic materials.

The liquid solvent can include DEG, TEG, DIPB, and the like. For example, the liquid solvent can include DEG. The liquid solvent can be a solvent and water mixture having a solvent concentration from a low of about 40 wt %, about 60 wt %, or about 75 wt % to a high of about 85 wt %, about 95 wt %, or about 99 wt % based on the weight of the mixture. For example, the liquid solvent can have a DEG concentration from a low of about 40 wt %, about 60 wt %, or about 75 wt % to a high of about 85 wt %, about 95 wt %, or about 99 wt % and a water concentration from a low of about 1 wt %, about 5 wt %, or about 15 wt % to a high of about 25 wt %, about 40 wt %, or about 60 wt % based on the weight of the liquid solvent.

The liquid solvent can be introduced to the solvent absorption unit 286 of the sorption unit 226 at a mass flow rate ratio of solvent (in kilograms) to separated spent air (in kilograms) from a low of about 1:1, about 3:1, or about 5:1 to a high of about 10:1, about 15:1, or about 20:1. The solvent can be introduced to the solvent absorption unit 286 at a temperature from a low of about −50° C., about −20° C., about −10° C., about −5° C., about −1° C., or about 1° C. to a high of about 4° C., about 6° C., about 8° C., about 15° C., about 30° C., or about 50° C. and a pressure from a low of about 10 kPag, about 50 kPag, about 100 kPag, about 150 kPag, or about 250 kPag to a high of about 500 kPag, about 600 kPag, about 700 kPag, about 1,000 kPag, or about 1,500 kPag.

The solvent absorption unit 286 can include one or more vessels for contacting the separated spent air with one or more liquid solvents. For example, the solvent absorption unit 286 can be or include one or more columns (not shown) for gas-liquid contacting. The column can be empty, partially filled, or completely filled with one or more materials to improve mass transfer and/or separation of the VOCs from the separated spent air. For example, the fill material can include, but is not limited to, structured materials, random packed materials, trays, or any combination thereof. Two or more types of fill material can be disposed within the column. For example, the column can contain random dumped packing and one or more trays.

The liquid solvent can be introduced into an upper portion of the column of the solvent absorption unit 286 and the separated spent air can be introduced into the lower portion of the column. The separated spent air can rise in the column and come into contact with the falling liquid solvent. The falling liquid solvent can absorb VOCs in the separated spent air to obtain or produce a residual VOC containing spent air in line 287. For example, the liquid solvent can absorb non-aromatics, cumene, benzene, toluene, and any combination or mixture thereof from a low of about 10 ppmw, about 100 ppmw, about 500 ppmw, or about 1,000 ppmw to a high of about 0.2 wt %, about 0.6 wt %, about 1 wt %, about 5 wt %, or about 10 wt % based on the total weight of non-aromatics, cumene, benzene, and/or toluene in the separated spent air introduced to the column of the sorption unit 126. The liquid solvent can absorb methanol and/or formic acid from a low of about 1 ppmw, about 5 ppmw, about 10 ppmw, or about 50 ppmw to a high of about 100 ppmw, about 500 ppmw, 1,000 ppmw, or about 2,500 ppmw based on the total weight of methanol and/or formic acid in the separated spent air introduced to the column of the sorption unit 126. The column of the sorption unit 126 can be operated under a temperature from a low of about −50° C., about −20° C., about −10° C., about −5° C., or about 0° C. to a high of about 6° C., about 10° C., about 20° C., about 35° C., or about 50° C. and a pressure from a low of about 10 kPag, about 50 kPag, about 100 kPag, or about 200 kPag to a high of about 500 kPag, about 600 kPag, about 700 kPag, or about 1,500 kPag.

The VOC containing spent air in line 287 can then be introduced to the solid adsorbent unit 288 filled with activated carbon or zeolitic materials. The activated carbon can include powdered activated carbon, granular activated carbon, extruded activated carbon, bead activated carbon, impregnated activated carbon, polymer activated carbon, or any other composition containing activated carbon. In one or more embodiments, the solid adsorbent unit 288 can include one or more activated carbon beds in a parallel or series arrangement. The loading of the VOCs on the activated carbon beds in VOCs (in kilograms) to carbon (in kilograms) can be from a low of about 1:10, about 2:10, or about 3:10 to a high of about 5:10, about 6:10, or about 7:10. The solid adsorbent unit 288 can have any number of activated carbon beds. For example, the solid adsorbent unit 288 can have from a low of 1, 2, or 3 to a high of 5, 8, or 10 carbon beds. In another example, the solid adsorbent unit 288 can include from 1 to 6 carbon beds or from 2 to 4 carbon beds.

In one or more embodiments, the solid adsorbent can include molecular sieves, zeolitic materials, activated alumina, silica gels, alumina-silica gels, naturally occurring clays. In one or more embodiments, the solid adsorbent unit 288 can include one or more zeolite beds. The loading of the VOCs on the zeolite beds in VOCs (in kilograms) to zeolite (in kilograms) can be from a low of about 1:10, about 2:10, or about 3:10 to a high of about 5:10, about 6:10, or about 7:10. The solid adsorbent unit 288 can have any number of zeolite beds. The solid adsorbent unit 288 can have from a low of 1, 2, or 3 to a high of 5, 8, or 10 zeolite beds. In another example, the solid adsorbent unit 288 can include from 1 to 6 zeolite beds or from 2 to 4 zeolite beds.

The solid adsorbent can be operated under a temperature from a low of about −20° C., about 0° C., about 10° C., about 20° C., or about 30° C. to a high of about 40° C., about 50° C., about 60° C., about 80° C., or about 100° C. and a pressure from a low of about 1 kPag, about 5 kPag, about 10 kPag, about 20 kPag, or about 30 kPag to a high of about 40 kPag, about 50 kPag, about 60 kPag, about 80 kPag, or about 100 kPag.

The scrubbed air in line 228 can include oxygen in an amount from a low of about 1 wt %, about 4 wt %, or about 6 wt % to a high of about 8 wt %, about 12 wt %, or about 20 wt %. For example, the scrubbed air in line 228 can have an oxygen concentration from about 2 wt % to about 15 wt %, about 3 wt % to about 12 wt %, or about 1 wt % to about 8 wt %. The scrubbed air in line 228 can include nitrogen in an amount from a low of about 60 wt %, about 70 wt %, or about 80 wt % to a high of about 90 wt %, about 95 wt %, or about 99 wt %. For example, the scrubbed air in line 228 can have a nitrogen concentration from about 75 wt % to about 99 wt %, about 85 wt % to about 95 wt %, or about 92 wt % to about 98 wt %. The scrubbed air in line 228 can include non-aromatics, cumene, benzene, and/or toluene in an amount from a low of about 10 ppmw, about 25 ppmw, or about 40 ppmw to a high of about 50 ppmw, about 75 ppmw, or about 100 ppmw. For example, the scrubbed air in line 228 can have a non-aromatics/cumene/benzene/toluene concentration from about 10 ppmw to about 100 ppmw, about 25 ppmw to about 75 ppmw, or about 40 ppmw to about 60 ppmw. The scrubbed air in line 228 can include methanol and/or formic acid in an amount from a low of about 1 ppmw, about 3 ppmw, or about 5 ppmw to a high of about 10 ppmw, about 15 ppmw, or about 30 ppmw. For example, the scrubbed air in line 228 can have a methanol/formic acid concentration from about 1 ppmw to about 30 ppmw, about 3 ppmw to about 15 ppmw, or about 5 ppmw to about 10 ppmw.

The scrubbed air in line 228 can have a temperature from a low of about −20° C., about −10° C., about −5° C., about 0° C., or about 10° C. to a high of about 20° C., about 25° C., about 30° C., about 40° C., or about 50° C. The scrubbed air in line 228 can be at a pressure from a low of about 1 kPag, about 5 kPag, about 10 kPag, about 25 kPag, or about 40 kPag to a high of about 50 kPag, about 75 kPag, about 100 kPag, about 150 kPag, or about 500 kPag.

The scrubbed air in line 228 can be introduced to the bioreactor 230. The bioreactor 230 can include one or more biofilters, each containing biological material. The bioreactor 230 can direct flow of the scrubbed air in line 228 through a biological material of the bioreactor 230 to obtain or produce a final discharge or clean air in line 232.

The biological material in the bioreactor 230 can include, but is not limited to, activated sludge, algae, microbes, and the like. The biological material can remove any trace amounts of VOCs, including non-aromatics, cumene, benzene, toluene, methanol, and formic acid, present in the scrubbed air. For example, the biological material can remove at least about 50 wt %, at least about 75 wt %, at least about 85 wt %, at least about 90 wt %, at least about 95 wt %, at least about 99 wt %, at least about 99.99 wt %, or 100% of the non-aromatics, cumene, benzene, and/or toluene present in the scrubbed air introduced to the biological reactor 230. The biological material can remove at least about 50 wt %, at least about 75 wt %, at least about 85 wt %, at least about 90 wt %, at least about 95 wt %, at least about 99 wt %, at least about 99.99 wt %, or 100% of the methanol and/or formic acid in the scrubbed air introduced to the biological reactor 230. The biological reactor can be operated under a temperature from a low of about −30° C., about −15° C., about 0° C., about 10° C., or about 20° C. to a high of about 25° C., about 35° C., about 45° C., about 60° C., or about 75° C. and a pressure from a low of about 1 kPag, about 3 kPag, or about 5 kPag, to a high of about 7 kPag, about 10 kPag, about 12 kPag, about 15 kPag, or about 20 kPag. In one or more embodiments, the biological reactor 230 can operate without an external heat source and without downstream incineration.

The biological material can be replenished via make-up, addition, or circulation of biological sludge from an activated sludge unit 290, for example. The activated sludge unit 290 can include an aeration tank or vessel (not shown) and a settling tank (not shown). The activated sludge unit can receive at least a portion of the waste water via line 245 produced from the cumene oxidation process disclosed herein. The waste water via line 245 can have a methanol concentration from a low of about 0.10 wt %, about 0.20 wt %, about 0.25 wt %, about 0.30 wt %, or about 0.34 wt % to a high of about 0.36 wt %, about 0.40 wt %, about 0.45 wt %, about 0.50 wt %, or about 0.60 wt %. The waste water can be aerated or mixed with a molecular oxygen containing gas, such as air, in the activated sludge unit 290 to obtain or produce aerated waste water. In the activated sludge unit 290 one or more organisms, such as bacteria, can be mixed or otherwise combined with the waster water before, during, or after mixing with the molecular oxygen containing gas resulting an aerated mixture. The aerated mixture can then be introduced to a settling tank in the activated sludge unit 290 to obtain or produce the activated sludge. The settling tank can include one or more tanks, one or more vessels, one or more bodies of water, and/or one or more earthen pits.

The molecular oxygen containing gas can include, but is not limited to, air, oxygen, essentially oxygen, oxygen-enriched air, mixtures of oxygen and air, mixtures of air and/or oxygen with steam, mixtures of oxygen and one or more inert gases, for example, nitrogen and/or argon, or any combination thereof. For example, the molecular oxygen containing gas can contain about 20 vol % oxygen or more, about 30 vol % oxygen or more, about 40 vol % oxygen or more, about 50 vol % oxygen or more, about 60 vol % oxygen or more, about 65 vol % oxygen or more, about 70 vol % oxygen or more, about 75 vol % oxygen or more, about 80 vol % oxygen or more, about 85 vol % oxygen or more, about 90 vol % oxygen or more, about 95 vol % oxygen or more, or about 99 vol % oxygen or more. The organisms can include bacteria, yeast, and protozoa. The protozoa can include amoebae, spirotrichs, peritrichs, or vorticellids, or any combination thereof.

In an example, the biological material in the biological reactor 230 can be maintained or replenished via make-up, addition, or circulation of biological sludge via line 292 from the activated sludge unit 290. The activated sludge unit 290 can also receive waste water produced from the cumene oxidation process disclosed herein. For example, the activated sludge unit 290 can receive the waste water via line 245 as disclosed herein.

The clean air in line 232 can include oxygen in an amount from a low of about 1 wt %, about 4 wt %, or about 6 wt % to a high of about 8 wt %, about 12 wt %, or about 20 wt %. For example, the clean air in line 232 can have an oxygen concentration from about 2 wt % to about 15 wt %, about 3 wt % to about 12 wt %, or about 1 wt % to about 8 wt %. The clean air in line 232 can include nitrogen in an amount from a low of about 60 wt %, about 70 wt %, or about 80 wt % to a high of about 90 wt %, about 95 wt %, or about 99 wt %. For example, the clean air in line 232 can have a nitrogen concentration from about 75 wt % to about 99 wt %, about 85 wt % to about 95 wt %, or about 92 wt % to about 98 wt %.

The clean air in line 232 can include non-aromatics, cumene, benzene, and/or toluene in an amount from a low of 0 ppmw, about 0.0001 ppmw, or about 0.001 ppmw to a high of about 0.01 ppmw, about 0.05 ppmw, or about 0.1 ppmw. For example, the clean air in line 232 can have a non-aromatics/cumenelbenzeneitoluene concentration from 0 ppmw to about 0.075 ppmw, about 0.0001 ppmw to about 0.04 ppmw, or about 0.001 ppmw to about 0.02 ppmw.

The clean air in line 232 can include methanol and/or formic acid in an amount from a low of 0 ppmw, about 0.0001 ppmw, or about 0.001 ppmw to a high of about 0.01 ppmw, about 0.05 ppmw, or about 0.1 ppmw. For example, the clean air in line 232 can have a methanol/formic acid concentration from 0 ppmw to about 0.075 ppmw, about 0.0001 ppmw to about 0.04 ppmw, or about 0.001 ppmw to about 0.02 ppmw. The clean air in line 232 can contain essentially no NOx, non-aromatics/cumene/benzene/toluene, and/or methanol/formic acid. In an example, the clean air in line 232 can contain essentially no non-aromatics/cumene/benzene/toluene, and/or methanol/formic acid and contains no NOx. The clean air in line 232 can have a temperature from a low of about −10° C., about 0° C. about 10° C., about 15° C., or about 20° C. to a high of about 35° C., about 40° C.,or about 45° C., about 50° C., or about 55° C. The clean air in line 232 can be introduced to the atmosphere.

A method for purifying spent air, comprising: oxidizing cumene in the presence of an oxidant to produce an oxidized product comprising methanol and a spent air; separating the spent air from the oxidized product; contacting the spent air with an absorbent, an adsorbent, or a mixture thereof to remove at least a portion of any impurities in the spent air to produce a first purified air; and contacting the first purified air with a biological material to produce a treated air.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for purifying spent air, comprising:
   oxidizing cumene in the presence of an oxidant to produce an oxidized product comprising methanol and a spent air;
   separating the spent air from the oxidized product;
   contacting the spent air with an absorbent, an adsorbent, or a mixture thereof to remove at least a portion of any impurities in the spent air to produce a first purified air; and
   contacting the first purified air with a biological material to produce a treated air; wherein no supplemental water is injected into the spent air prior to the spent air being cooled.

2. The method of claim 1, wherein the treated air contains less than 1 ppmw volatile organic compounds, and further comprising:
   cooling the spent air after separating the spent air from the oxidized product; and
   separating water from the cooled spent air.

3. The method of claim 1, wherein the oxidant comprises air, oxygen, oxygen-enriched air, or combination thereof and wherein the spent air comprises molecular oxygen, nitrogen, water, methyl hydrogen peroxide, formic acid, benzene, toluene, and cumene.

4. The method of claim 1, further comprising separating water from the spent air prior to contacting the spent air with the absorbent, the adsorbent, or the mixture thereof.

5. The method of claim 1, wherein the adsorbent comprises at least one bed of zeolitic material, activated carbon, or both.

6. The method of claim 1, wherein the absorbent comprises a liquid solvent.

7. The method of claim 6, wherein the liquid solvent comprises diethylene glycol, triethylene glycol, diisopropylbenzene, or mixtures thereof.

8. The method of claim 1, further comprising:
   contacting the spent air with a liquid solvent to produce an absorbed air; and
   contacting the absorbed air with a solid adsorbent comprising at least one bed of zeolitic material, activated carbon, or both to produce the first purified air.

9. The method of claim 1, wherein the biological material comprises activated sludge, algae, microbial organisms, or mixtures thereof.

10. The method of claim 1, wherein the spent air comprises from about 5 wt % to about 30 wt % volatile organic compounds.

11. The method of claim 1, wherein the spent air and the treated air are essentially free from any NOx.

12. The method of claim 1, wherein the impurities in the spent air include volatile organic compounds that are selected from the group consisting of non-aromatics, cumene, benzene, toluene, methanol, and formic acid, and any mixture thereof.

13. A method for purifying spent air, comprising:
   introducing cumene and an oxidant to an oxidation unit to produce an oxidized product comprising about 10 wt % to about 40 wt % cumene hydro-peroxide and a spent air comprising molecular oxygen, water, methanol, formic acid, methyl hydrogen peroxide, benzene, toluene, non-aromatics, and cumene;
   introducing the spent air to a separation unit to produce a separated spent air comprising volatile organic compounds and a liquid phase component comprising cumene and water;
   contacting the separated spent air with a liquid solvent in a solvent absorption unit to produce a scrubbed air comprising about 10 ppmw to about 1,000 ppmw non-aromatics, cumene, benzene, and toluene and about 1 ppmw to about 500 ppmw methanol and formic acid; and
   introducing the scrubbed air to a bioreactor to produce a clean air, wherein the bioreactor includes a biological material and wherein the scrubbed air is at a temperature no greater than 50 degrees Celsius;
   wherein no supplemental water is injected into the spent air prior to the spent air being cooled.

14. The method of claim 13, wherein the clean air contains less than 1 ppmw volatile organic compounds.

15. The method of claim 13, wherein the liquid solvent comprises diethylene glycol, triethylene glycol, diisopropylbenzene, or mixtures thereof and wherein the biological material included within the bioreactor comprises activated sludge, algae, microbes, or mixtures thereof.

16. The method of claim 13, wherein the spent air and the clean air are essentially free from any NOx.

17. A method for purifying spent air, consisting essentially of:
   introducing cumene and an oxidant to an oxidation unit to produce an oxidized product comprising about 10 wt % to about 40 wt % cumene hydro-peroxide and a spent air comprising molecular oxygen, water, methanol, formic acid, methyl hydrogen peroxide, benzene, toluene, non-aromatics, and cumene;
   introducing the spent air to a condenser to produce a cooled spent air;
   introducing the cooled spent air to a separation unit to produce a separated spent air comprising volatile organic compounds and a liquid phase component comprising cumene and water;
   introducing the separated spent air to a solvent absorption unit to produce a scrubbed air comprising about 10 ppmw to about 1,000 ppmw non-aromatics, cumene, benzene, and toluene and about 1 ppmw to about 500 ppmw methanol and formic acid;
   introducing the scrubbed air to a bioreactor to produce a clean air having less than 1 ppmw total concentration of volatile organic compounds selected from the group consisting of: non-aromatics, cumene, benzene, toluene, methanol, and formic acid;
   introducing the oxidized product to a cleavage unit to produce a crude product comprising acetone and phenol; and
   introducing a waste water containing at least a portion of the crude product to an activated sludge unit.

18. The method of claim 17, wherein the spent air comprises about 10 ppmw to about 5,000 ppmw methanol, methyl hydrogen peroxide, and formic acid, about 5 wt % to about 30 wt % nonaromatics, cumene, benzene, and toluene, and about 1 wt % to about 8 wt % molecular oxygen.

19. The method of claim 17, wherein a biological material included within the bioreactor comprises activated sludge, algae, microbes, or mixtures thereof.

20. The method of claim 17, wherein the spent air and the clean air are essentially free from any NOx.

\* \* \* \* \*